United States Patent [19]
Igeta et al.

[11] Patent Number: 6,045,262
[45] Date of Patent: Apr. 4, 2000

[54] APPARATUS AND METHOD FOR CONTROLLING TABLE IN MEDICAL DIAGNOSIS SYSTEM

[75] Inventors: Yoshikazu Igeta, Matsudo; Eiichi Makino, Kashiwa; Mikio Mochitate, Noda; Hiroshi Abe, Kashiwa; Takeshi Yano, Kagoshima, all of Japan

[73] Assignee: Hitachi Medical Corporation, Tokyo, Japan

[21] Appl. No.: 09/044,226

[22] Filed: Mar. 19, 1998

[30] Foreign Application Priority Data

Mar. 19, 1997 [JP] Japan .................................. 9-085774

[51] Int. Cl.[7] ...................................................... A61B 6/04
[52] U.S. Cl. ............................................. 378/209; 318/649
[58] Field of Search ..................................... 378/209, 205, 378/208, 114; 318/560, 566, 625, 626, 652, 265, 286, 467, 486, 649

[56] References Cited

U.S. PATENT DOCUMENTS 5,467,002  11/1995  Brooks ..................................... 318/553

*Primary Examiner*—David P. Porta
*Assistant Examiner*—Michael J. Schwartz
*Attorney, Agent, or Firm*—Antonelli, Terry, Stout & Kraus, LLP

[57] ABSTRACT

A control apparatus for controlling movement of a table supporting an object under inspection in a medical diagnosis system includes a driving power unit for moving the table, a position detector for outputting a signal indicating a position of the table, a positioning servo-control unit for controlling the driving power unit so that the detected position signal coincides with a given desired value, a manipulating force detector for outputting a force signal corresponding to a manipulating force applied by an operator, a force-to-position conversion unit for converting the force signal into a position change quantity for the table, a force control unit for controlling the driving power unit in accordance with the position change quantity so long as the manipulating force is being detected, and a change-over unit for selecting either the positioning servo-control unit or the force control unit in response to operation of the operator.

18 Claims, 14 Drawing Sheets

APPARATUS AND METHOD FOR CONTROLLING TABLE IN MEDICAL DIAGNOSIS SYSTEM

BACKGROUND OF THE INVENTION

The present invention generally relates to a control apparatus for controlling position of a table or a bed for supporting an object or patient under inspection lying thereon in a medical diagnosis system such as an X-ray diagnosis system, X-ray computerized tomography system (hereinafter referred to as the X-ray CT system), magnetic resonance imaging (MRI) system and the like. More specifically, the invention is concerned with a table control apparatus for a medical diagnosis system which is designed for controlling movement or displacement of the table supporting a person under inspection lying thereon for the purpose of positioning an affected part of the person or for other purposes.

In the X-ray CT system which is a typical one of the medical diagnosis systems, inspection or diagnosis is performed in the state in which a patient (i.e., a person undergoing medical inspection, diagnosis or the like) is lying on a table. In order to carry out effectively the inspection or diagnosis and/or treatment, such a table positioning control is required that an electric motor constituting a driving power means for moving the table is driven under remote control, to thereby move or displace the table to a position close to an X-ray CT scanner carrying an X-ray tube, an X-ray detector, etc. In this conjunction, it is noted that such a combined procedure is often adopted in which inspection and treatment are carried out at a same time by combining the X-ray CT system and a circulatory organ X-ray inspection system capable of angiographic inspection because of a trend of the interventional radiography (IVR in abbreviation) such as e.g. transcatheter arterial embolization being increasingly conducted in recent years. In such combination system, it is desirable that one and the same table for supporting the person undergoing the inspection and the treatment in a lying state can be used for both the X-ray CT diagnosis and the angiographic treatment in order to allow the diagnosis and the treatment to be carried out consistently in continuation. Under the circumstances, there arises a demand for the table for the combination diagnosis system which is imparted with not only the function suited for the X-ray CT diagnosis but also the function proper to the angiographic treatment. Parenthetically, the table for the medical diagnosis system is required to ensure high-speed positioning with high accuracy, while the table for the angiographic inspection or treatment system is required to allow floating operation freely in two-dimensional directions.

The conventional table structure for the angiographic inspection or treatment can be manipulated by operator's hand freely in X- and Y-directions for carrying out the angiographic inspection or surgical operation. However, because of a large scale mechanism incorporated in the table structure, high load is encountered in manipulating the table, requiring a large manipulating force. Thus, the table for the angiographic treatment suffers a problem that the table is not easy to use for the interventional radiology which requires a fine or delicate positioning manipulation. Further, the conventional table control apparatus for the X-ray CT diagnosis is designed to satisfy the positioning control required in the X-ray CT diagnosis. In other words, in the conventional table control apparatus for the X-ray CT diagnosis, it is practically impossible to perform fine or delicate operation for moving the table to a given position desired by the operator by a hand required for manipulation of the interventional radiology.

Furthermore, in the apparatus for manually operating the table, a large manipulating force is required because of a load imposed additionally by weight of the patient. Besides, difficulty is encountered in stopping the table accurately at a desired position due to the influence of the inertial force. Thus, the conventional table control apparatus is not always easy to operate or manipulate.

SUMMARY OF THE INVENTION

In the light of the state of the art described above, it is an object of the present invention to provide a control apparatus for controlling a table of a medical diagnosis system, which apparatus includes a positioning servo-control system for controlling the table so as to maintain it at a predetermined desired position and a force control system for moving the table in accordance with a position change quantity corresponding to a manipulating force applied by an operator, wherein the positioning servo-control system and the force control system can be changed over in response to manipulating operation of the operator.

Another object of the present invention is to provide a control method for controlling the movement of a table in a medical diagnosis system.

In view of the above and other objects which will become apparent as the description proceeds, there is provided according to a general aspect of the present invention a control apparatus for controlling movement of a table supporting an object in a medical diagnosis system, which apparatus includes a driving power unit for moving the table in a predetermined direction, a position detector for outputting a position signal corresponding to a position of the table, a positioning servo-control system for controlling the driving power unit so that the position signal coincides with a given desired value, a manipulating force detector for outputting a force signal corresponding to a manipulating force applied by an operator, a force-to-position conversion unit for converting the force signal into a position change quantity for the table, a force control system for controlling the driving power unit in accordance with the position change quantity so long as the manipulating force of the operator is being detected, and a change-over unit for selecting either the positioning servo-control system or the force control system in response to operation of the operator.

By virtue of the above-mentioned arrangement of the table control apparatus for the medical diagnosis system, the function for positioning the table to a given position as desired through manual operation can be realized in addition to the high-speed table positioning function because of the provision of the table manipulating force control function, whereby the table provided with the control apparatus according to the present invention can find a wide range of applications in the medical field inclusive of photography, fluoroscopy, diagnosis, therapy and so forth. In particular, with the table control apparatus for the medical diagnosis system according to the invention, fine and delicate positioning of an affected part of a patient lying on the table can be realized for performing treatment by using a catheter or the like manually with a relatively small manipulating force even in the case where the table inclusive of the weight of the patient lying thereon presents a heavy load.

In a preferred mode for carrying out the present invention, such arrangement may be adopted that the positioning servo-control system and the manipulating force control system can be changed over in dependence on the function of the medical diagnosis system intended by the operator.

To say in another way, the table positioning control and the table manipulating force control can be effectuated independently and exchangeably.

In another preferred mode for carrying out the present invention, such arrangement may be adopted that operation of the manipulating force control system is imparted with higher priority than the positioning servo-control system.

By imparting high priority or preference level to the table manipulating force control over the table positioning control, the table can be moved with ease for taking out a person undergoing diagnosis from the CT-scanner in case of emergency even when the positioning control operation is being effected for the inspection with the X-ray CT system. Thus, enhanced safety can be ensured even in case of emergency.

In yet another preferred mode for carrying out the present invention, such arrangement may be adopted that the start of operation by the operator is detected and then the manipulating force is converted into a position change quantity with delay of a predetermined time from the detection of the start of operation by the operator. Additionally, when the conversion of the manipulating force into the position change quantity of the table is stopped in dependence on corresponding manipulation performed by the operator, then the force control operation is terminated with delay of a predetermined time from the stoppage of the conversion processing of the manipulating force. With the above arrangement, a delay time is involved in the change-over operation between the positioning servo-control and the manipulating force control, whereby lag in manipulation of the table due to inertia of the table and the driving power unit therefor can be compensated for.

In a further preferred mode for carrying out the invention, such arrangement may be adopted in conjunction with the force control that a value of the manipulating force detected initially is set to zero and then difference in value between a manipulating force detected at first after the zero setting and a manipulating force detected in secession is converted into the position change quantity. By virtue of the above arrangement, sudden movement of the table can be suppressed even when a large manipulating force is applied to the table immediately after the change-over to the force control.

The above and other objects, features and attendant advantages of the present invention will more easily be understood by reading the following description of the preferred embodiments thereof taken, only by way of example, in conjunction with the accompanying drawings.

BRIEF DESCRIPTION OF THE DRAWINGS

In the course of the description which follows, reference is made to the drawings, in which.

DESCRIPTION OF THE PREFERRED EMBODIMENTS

Figure 1A:
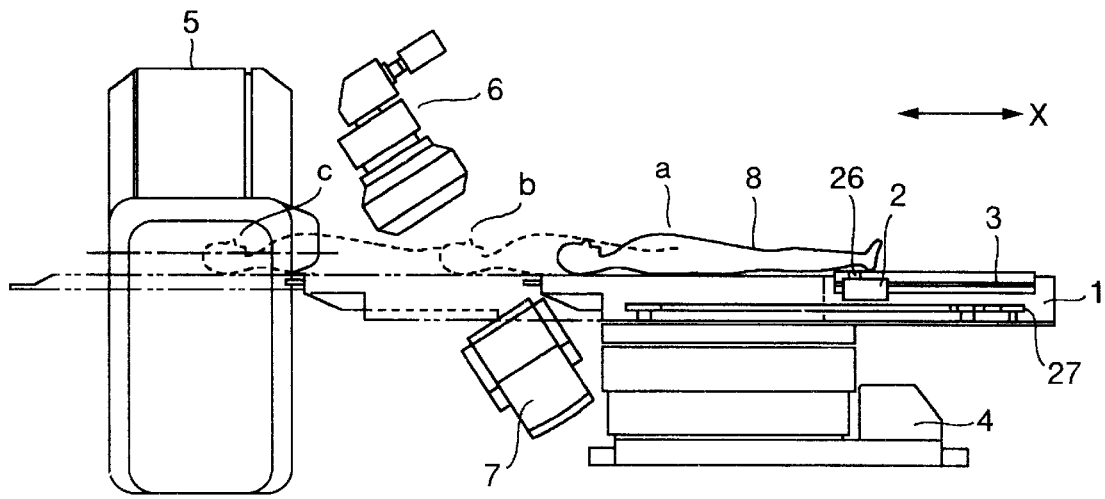
FIG. 1(A) is a side elevational view showing schematically a structure of a diagnosis system which includes a combination of an X-ray CT system and an angiography system in which a table control apparatus according to a first embodiment of the present invention is employed.

Now, the present invention will be described in detail in conjunction with what is presently considered as preferred or typical embodiments thereof by reference to the drawings. In the following description, like reference characters designate like or corresponding parts throughout the several views.

Embodiment 1

Figure 1B:
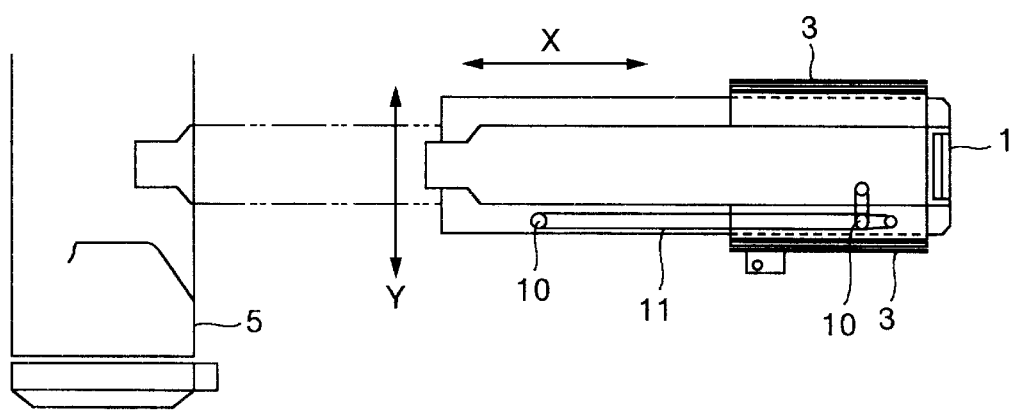
FIG. 1(B) is a top plan view showing the same system.
Figure 1C:
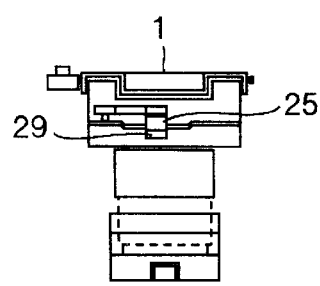
FIG. 1(C) is an end view of the same as viewed from right-hand side in FIG. 1(A)

FIGS. 1(A), 1(B) and 1(C) are views showing a structure of a combined diagnosis system which includes a combination of an X-ray CT (computerized tomography) system and an angiographic inspection/treatment system to which the present invention is applied. Referring to FIG. 1(A) which shows the diagnosis system in a side elevational view, reference numeral 5 denotes a scanner unit of the X-ray CT system, numeral 6 denotes an X-ray tube of the angiographic inspection system/treatment, and numeral 7 denotes an image intensifier of the same. The X-ray tube 6 and the image intensifier 7 are supported by a supporting mechanism generally referred to as the C-arm, although illustration thereof is omitted. Further, reference numeral 1 denotes a table structure (referred to simply as the table) which is provided in common to both the X-ray CT system and the angiographic inspection/treatment system, and reference numeral 2 denotes a manipulation unit which is comprised of a manipulating force sensor 26, a sensor output amplifier (not shown) and others. The manipulation unit 2 is designed for detecting the manipulating force applied by the operator. In this diagnosis system, the table 1 may be so moved that the person 8 who is going to undergo diagnosis or inspection (hereinafter referred to as the person under inspection or so) is displaced from, for example, a position a or b to a predetermined target or desired position (position for measurement) c aligned with the scanner 5 of the X-ray CT system, whereon the person 8 under inspection is diagnosed to identify discriminatively or specify an affected part. After the CT inspection, the table 1 on which the person 8 is lying is then moved to a position which is positionally aligned with the X-ray tube 6 and the image intensifier 7 of the angiography system and set stationarily at the position b. At this position, a catheter may be inserted into a blood vessel of the person 8 under inspection to thereby conduct a medical treatment or inspection while confirming the position or location of the catheter with the aid of the angiography system.

In order to position the table 1 precisely at the position b after displacement of the table 1 from the position c, a fine control of the table 1 is required. To this end, a manipulating force applied to the manipulation unit 2 by the operator is detected by the manipulating force sensor (load cell) 26 of the manipulation unit 2. The detection output signal of the manipulating force sensor 26 is fed back to a control unit described hereinafter to carry out a fine or delicate control for positioning the table and hence the person 8 under inspection at the position c with high accuracy.

FIG. 1(B) is a top plan view showing schematically the table 1. As can be seen from this figure, the table 1 is provided with a mechanism capable of moving the table 1 in the X-direction and the Y-direction independently of each other within a predetermined range of displacement (although the mechanism is not shown). In FIGS. 1A and 1(B), reference numeral 3 denotes a rail on which the manipulation unit 2 is mounted movably therealong, and numeral 4 denotes a table control unit in which electronic circuits for controlling displacement and positioning of the table 1 are accommodated. In this conjunction, the rail 3 should preferably be disposed at each side of the table 1 so that the manipulation unit 2 can be installed at a position which facilitates manipulation of the unit 2 by the operator regardless whether he or she stands at any side of the table 1. As mentioned previously, the manipulation unit 2 includes the manipulating force detecting sensor (load cell) 26. Further, a table position detector 27 is provided for detecting the position of the table 1 for the positional control thereof.

In the case of the instant embodiment of the invention, a potentiometer is employed as the table position detector 27, wherein such arrangement is adopted that the potentiometer cooperates with a driving system including a pulley 10, a power transmission belt 11 and other for detecting the position of the table. An electric motor 25 serving as a driving power means or unit has an output shaft to which an encoder 29 is operatively coupled for detecting the rotation speed of the motor. Taking as example the Y-coordinate mechanism for the table 1 (i.e., mechanism for displacing the table 1 in the Y-direction), the encoder 29 and the motor 25 are mounted in such disposition as illustrated in FIG. 1(C). Parenthetically, FIG. 1(C) is a side elevational view of the diagnosis system as viewed in the X-direction in FIG. 1(A) (i.e., viewed from the right-hand side in FIG. 1(A)). As a mechanism for transmitting the driving force of the motor 25 to the table 1, it is assumed, only by way of example, that the transmission mechanism constituted by the pulleys 10 and the power transmission belt 11 is employed, as mentioned above.

Figure 2:
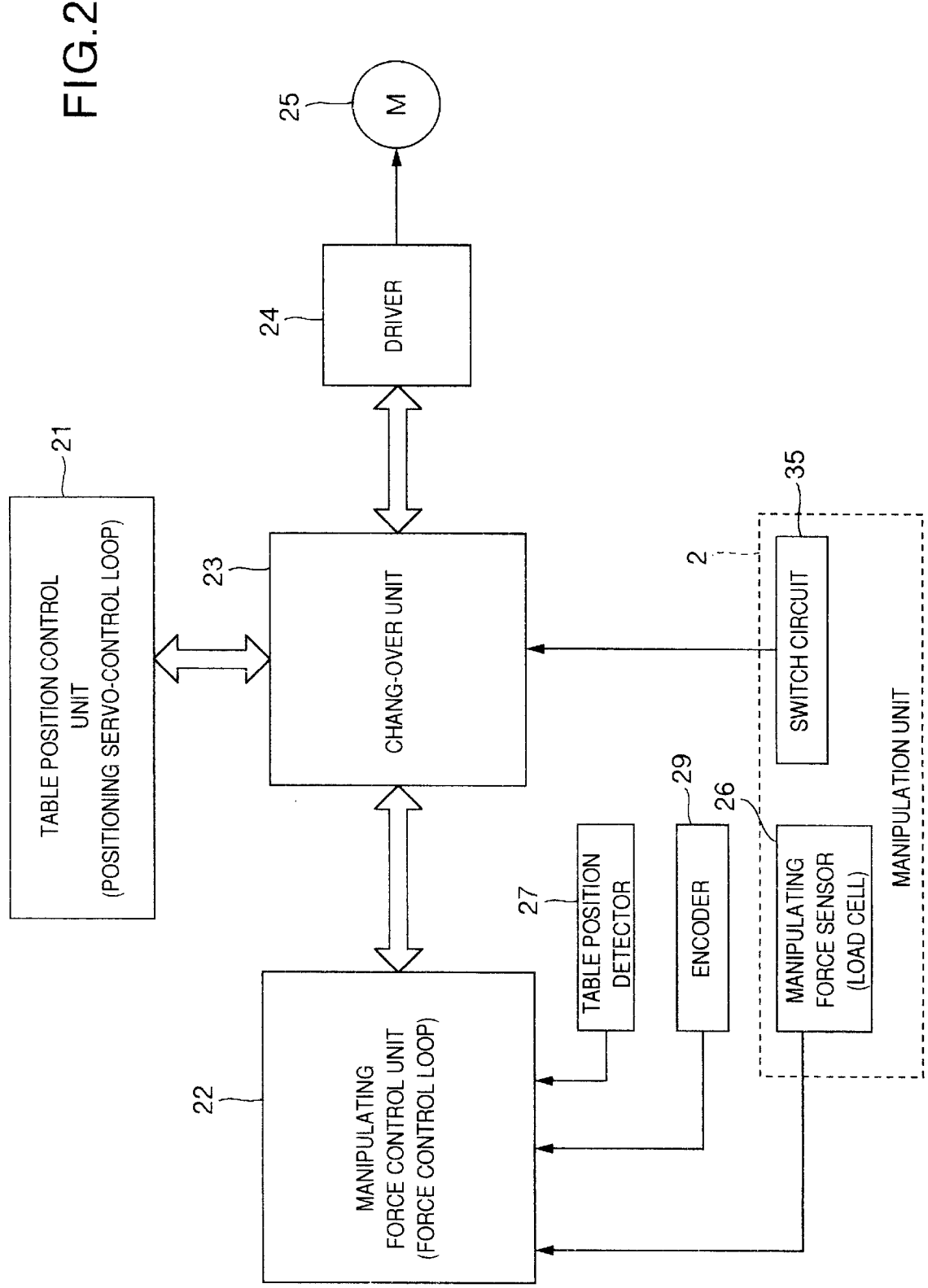
FIG. 2 is a block diagram showing generally and schematically a system configuration of a control apparatus according to an embodiment of the invention for controlling displacement/positioning of a table in the medical diagnosis system shown in FIG. 1.

FIG. 2 shows a configuration of the control apparatus for controlling displacement/positioning of the table 1 according to the first embodiment of the invention. Referring to the figure, the control apparatus includes as main components a table position control unit 21 adapted to be put into operation primarily for taking X-ray CT-images, a manipulating force control unit 22 for manually operating the table 1 primarily for the inspection by using the angiography system, a change-over unit 23 for changing over the control operation between the table position control unit 21 and the manipulating force control unit 22, and a motor driver 24 for driving the motor 25 adapted for driving the table 1 on the basis of amplified output signal of the table position control unit 21 or that of the manipulating force control unit 22. Further, the manipulating force sensor 26, the table position detector 27 and the encoder 29 for detecting the rotation speed of the motor 25 mentioned hereinbefore also constitute parts of the control apparatus shown in FIG. 2.

In case the X-ray CT-images are to be taken, positioning control of the table 1 is performed with high accuracy in order to move and position automatically the person 8 under inspection at the predetermined target (desired) position c. For effectuating the positioning control now of concern, the output signal of a positioning servo-control loop of the table position control unit 21 is inputted to the motor driver 24 by way of the change-over unit 23. In this case, however, the output signal of the force control loop of the manipulating force control unit 22 is not transmitted to the motor driver 24. Through this positioning servo-control, the motor 25 is driven at a constant speed to thereby move the person 8 under inspection to the predetermined target position c, whereupon the movement of the table 1 is stopped.

On the other hand, in the case of the angiographic inspection or treatment, the manipulation unit 2 is manually operated by the operator. More specifically, when the operator places his or her hand on the manipulation unit 2 and applies pressure higher than a predetermined level, a manipulating force detection start switch 35 incorporated in the manipulation unit 2 generates a signal indicating the start of manipulation, which signal is then supplied to the change-over unit 23. The manipulating force control unit 22 responds to the manipulation start signal to output a signal which is coupled to the input of the motor driver 24. In that case, however, the output signal of the positioning servo-control loop of the table position control unit 21 is not transmitted to the motor driver 24. Furthermore, when the operator applies a force to the manipulation unit 2 in a desired direction (X-Y-direction), magnitude of the manipulating force as well as direction thereof is detected by the manipulating force sensor (load cell) 26. Subsequently, magnitude of the positional displacement of the table to be realized (referred to also as the position change quantity) as well as the direction thereof corresponding to the manipulating force detected by the manipulating force sensor 26 is determined by the manipulating force control unit 22. The signal representing the magnitude of the positional displacement (i.e., position change quantity) as well as the direction thereof is inputted to the driver 24 by way of the change-over unit 23, as a result of which the motor 25 is driven in conformance with the position change quantity and the direction thereof. The operator adjusts the manipulating force applied to the manipulation unit 2 while visually confirming the position of the person 8 under inspection so that the person 8 and hence the table 1 can stop at the desired target position b.

Next, structures and operations of the manipulation unit 2, the manipulating force control unit 22, the table position control unit 21 and the change-over unit 23 will be described in more detail by referring to the drawings.

Figure 3A:
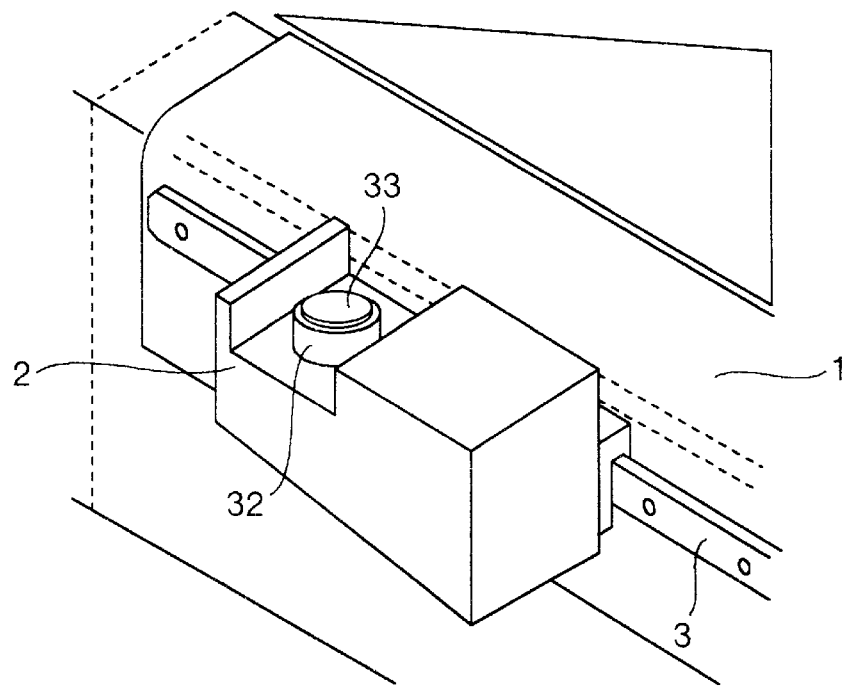
FIG. 3(A) is a perspective view showing an outer appearance of a manipulation unit constituting a part of the control apparatus.
Figure 3B:
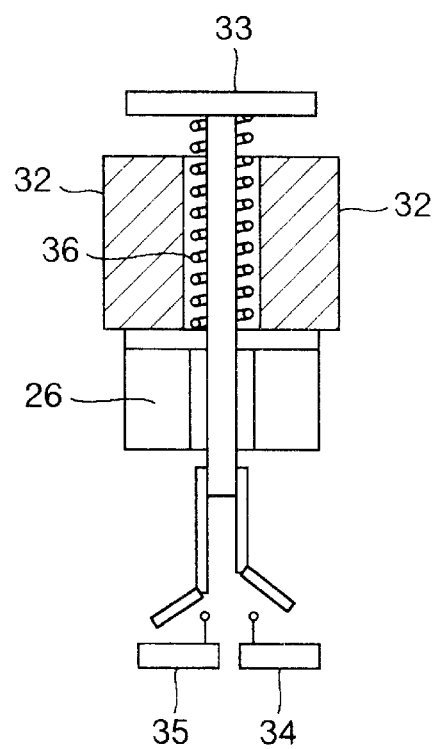
FIG. 3(B) is a schematic sectional view showing a manipulating force detector incorporated in the manipulation unit in a state where no manipulating force is applied.
Figure 3C:
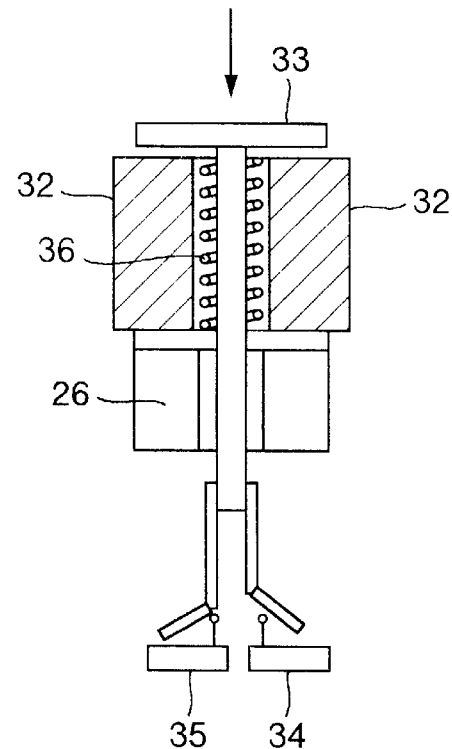
FIG. 3(C) is a view similar to FIG. 3(B) and shows the same in the state where a manipulating force is applied.

FIGS. 3(A), 3(B) and 3(C) are views showing schematically the manipulation unit 2 and the manipulating force sensor or detector thereof, respectively. More specifically, FIG. 3(A) shows an outer appearance of the manipulation unit 2, while FIGS. 3(B) and 3(C) are views showing a structure of a manipulating force detector incorporated in the manipulation unit 2. In FIG. 3(B), the manipulating force detector is shown in the state where no manipulating force is applied to the manipulation unit 2 by the operator, while in FIG. 3(C), the manipulating force detector is shown in the state where a manipulation force is applied. Referring to FIGS. 3(A), 3(B) and 3(C), the manipulation unit 2 is comprised of a load cell 26 serving as the sensor for detecting the manipulating force, a manipulation knob 32, a push button 33, a manipulating force zero point detecting switch 34 and a manipulating force detection start switch 35. The manipulating force zero point detecting switch 34 and the manipulating force detection start switch 35 are disposed in such positional relation that as the operator depresses the push button 33, the manipulating force detection start switch 35 is first actuated, which is then followed by actuation of the manipulating force zero point detecting switch 34 with some temporal delay, as can be appreciated from FIG. 3(C).

The push button 33 is implemented in such a structure that the operator can grip the knob 32 and simultaneously press the push button 33 downwardly (i.e., depress the push button 33). On the contrary, when the operator detaches his or her hand from the push button 33, the latter can resume the original position (i.e., the state shown in FIG. 3(B)) under the action of a return spring 36 disposed internally in the knob 32.

The manipulating force sensor or load cell 26 may be constituted by a strain gauge sensor which outputs an electric signal in correspondence to a pressure or force as applied. The manipulating force applied by the operator is transmitted to the load cell 26 by way of the knob 32. The load cell 26 detects the manipulating force applied thereto by the operator as two components in the orthogonal directions (i.e., X- and Y-directions), respectively, whereby a corresponding electric signal representing the force components in the respective directions is outputted from the load cell 26.

Now, let's assume that the operator desires to move the table 1. In that case, the operator grips the knob 32 and at the same time depresses the push button 33 (see FIG. 3(C)).

Figure 4:
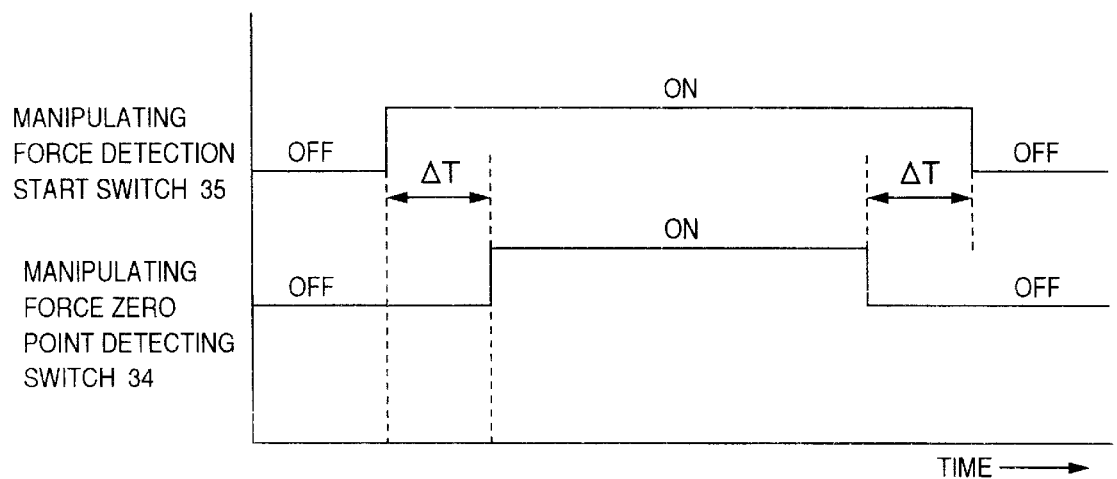
FIG. 4 is a timing chart for illustrating an operation timing of a manipulating force detection start switch and a manipulating force zero point detecting switch provided in association with a manipulation unit of the control apparatus.

When the push button 33 is depressed (i.e., applied with pressure in the downward direction), the manipulating force zero point detecting switch 34 and the manipulating force detection start switch 35 which are operatively coupled to the push button 33 are closed. At this juncture, it should be recalled that these two switches 34 and 35 are so implemented that the manipulating force detection start switch 35 is first closed in response to depression of the push button 33 and subsequently the manipulating force zero point detecting switch 34 is closed with a delay. In that case, a temporal deviation $\Delta T$ occurs between the signal outputted from the manipulating force detection start switch 35 and the signal generated by the manipulating force zero point detecting switch 34, as can be seen in FIG. 4. In other words, temporal difference or deviation $\Delta T$ intervenes between operation of the manipulating force zero point detecting switch 34 and that of the manipulating force detection start switch 35. Consequently, upon return operation of the push button 33, the manipulating force zero point detecting switch 34 is first opened, which is then followed by the opening of the manipulating force detection start switch 35 after lapse of the deviation time $\Delta T$ (i.e., with the time delay $\Delta T$).

The reason why the deviation or difference is provided between the actuation time points of the manipulating force zero point detecting switch 34 and the manipulating force detection start switch 35 is to absorb or cancel out delay involved in the operation of the table due to inertia of the table and that of the motor driving system upon changing-over of the control operation between the positioning servo-control loop and the force control loop. The relations between these switches and the control loops mentioned above will be described hereinafter in more detail.

Figure 8:
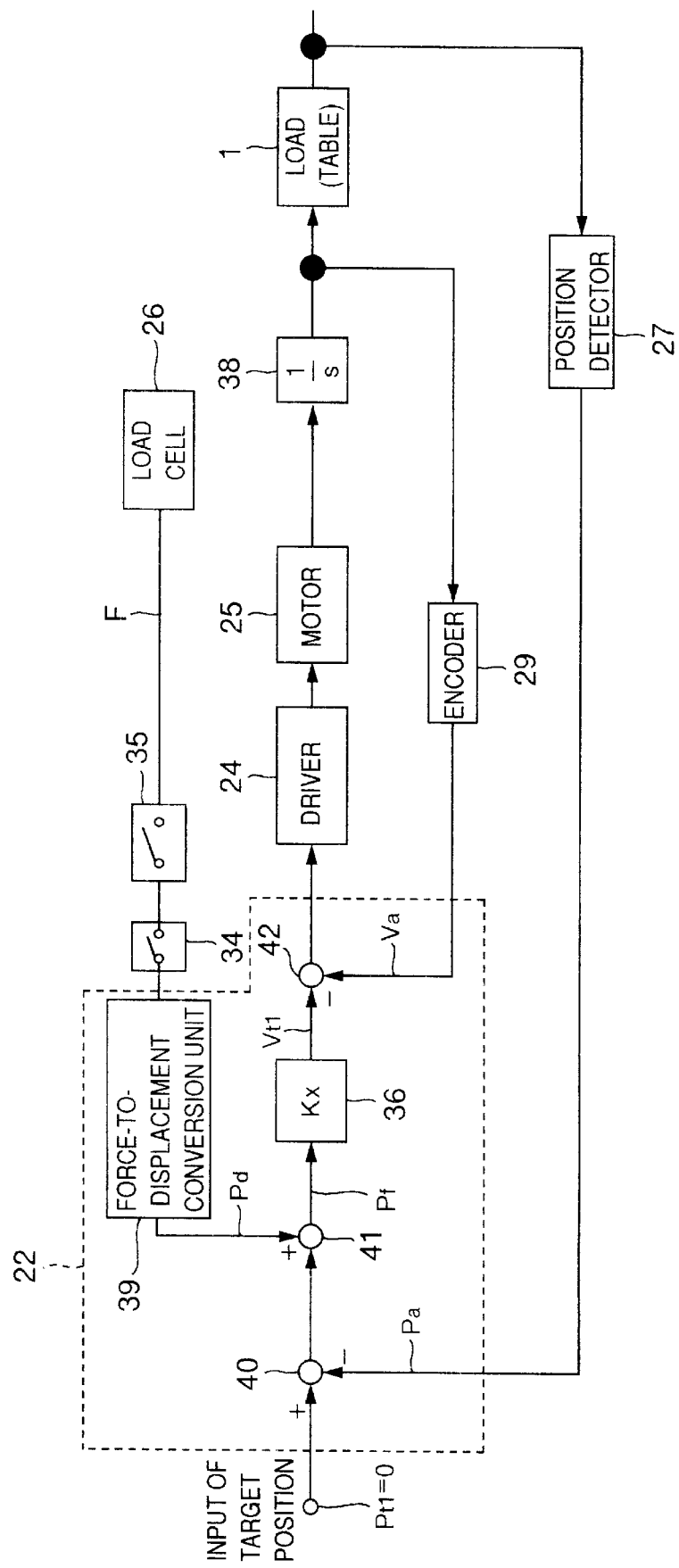
FIG. 8 is a block diagram showing a manipulating force control system or loop for performing a manipulating force control in the control apparatus according to the first embodiment of the invention.

Next, description will be directed to the force control loop of the manipulating force control unit 22 by reference to a block diagram shown in FIG. 8. Referring to the figure, the positioning servo-control loop is constituted by an input unit through which a target position ($Pt_1$) indicating signal is inputted, a positioning servo-amplifier 37, the motor driver 24, the motor 25, an integrator 38, the load (or table) 1, the table position detector 27 and the encoder 29. The positioning servo-control loop is designed to control the operation of the driving motor 25 such that deviation between the target position and the actual position of the load (table) 1 can be maintained zero. On the other hand, the load cell 26, the manipulating force detection start switch 35, the manipulating force zero point detecting switch 34 and a force-to-displacement conversion unit 39 constitute a system or circuitry for converting the manipulating force applied by the operator into magnitude of positional displacement of the table 1 (position change quantity). The circuitry mentioned just above is additionally in charge of controlling the change-over between the manipulating force control loop 22 and the table position control loop 21. Parenthetically, it should be mentioned that each of the manipulating force detection start switch 35 and the manipulating force zero point detecting switch 34 may be constituted by a micro-switch for mechanically turning on/off the signal path or alternatively by an electronic element generating a binary (low- or high-level) signal in dependence on the manipulation of the push button 33.

In the force control loop shown in FIG. 8, when the switch 35 or 34 is opened with the output Pd of the force-to-displacement conversion unit 39 being zero, the table 1 is so controlled as to be maintained at the current position. In the force control system, the input target position $Pt_1$ is set to zero. Difference between the current position Pa of the table 1 as detected by the table position detector 27 and the target position ($Pt_1=0$) is outputted to an adder 40. In other words, the current position indicating signal Pa is inputted to the control loop intact as the target or desired value. Difference between the signal ($Vt_1$) amplified with a gain Kx by the positioning servo-amplifier 37 and the negative feedback signal (Va) indicative of the motor speed as detected by the encoder 29 is arithmetically determined by an adder 42. The control loop constituted by the motor driver 24, the motor 25, the integrator 38 and the encoder 29 serves as a speed servo-control loop which operates to maintain the motor speed at a desired speed $Vt_1$ corresponding to the input target position signal $Pt_1$. Thus, when the table 1 is subject to some external force, the motor 25 is controlled by the negative feedback signal of the table position detector 27 such that the table 1 is maintained at the current position Pa nevertheless of external disturbance.

In the case of the angiographic inspection or treatment, the operator has to manipulate the manipulation unit 2 to thereby move the table 1 to the desired position (e.g. position b shown in FIG. 1(A)) and stop the table 1 at that position. Assuming now that both the switches 35 and 34 are closed as a result of operation of the manipulation unit 2 by the operator, a signal F indicating a manipulating force applied by the operator and detected by the load cell 26 is inputted to the force-to-displacement conversion unit 39. In response to the input of the manipulating force signal F, the force-to-displacement conversion unit 39 outputs a positional displacement signal Pd which corresponds to the manipulating force signal F. To this end, the force-to-displacement conversion unit 39 incorporates a memory (not shown) in which a data table containing coefficients for the conversion of the manipulating force signal F to the positional displacement Pd is stored. The relations between the manipulating forces F and the positional displacements Pd (conversion coefficients and the characteristics thereof) are experimentally determined in advance so as to be optimal. Difference Pf between the positional displacement signal Pd outputted from the force-to-displacement conversion unit 39 and the current position signal Pa outputted from the table position detector 27 is determined by the adder 41. A signal indicating the desired speed $Vt_1$ which corresponds to the difference value Pf is outputted from the amplifier 36. Consequently, the motor 25 moves the table 1 for a distance corresponding to the positional displacement Pd derived from the output of the force-to-displacement conversion unit 39. In this way, the operator can move the table 1 to a desired position and stop the table 1 at that position by regulating the manipulating force applied to the knob 32 of the manipulation unit 2. At the beginning of displacement of the table 1, the operator may encounter a relatively large load in his or her manipulation of the knob 32 because the positioning servo-control loop shown in FIG. 8 is operating. However, as the table 1 starts to move, displacement of the table 1 to the desired position can be realized with a very small force. Thus, the operator can move the table to the desired or target position smoothly and comfortably.

Parenthetically, the manipulating force control unit 22 indicated as enclosed in a broken line block in the force control system shown in FIG. 8 may be implemented by a microcomputer which is commercially available. The microcomputer includes an input/output interface, an analogue-to-digital (A/D) converter for converting analogue signals to digital signals, a memory unit for storing a control program and coefficient data, and a CPU (Central Processing Unit) for executing signal processings in accordance with the control program. However, it goes without saying that the functions of the manipulating force control unit 22 may be realized by employing hardware circuit elements in place of the microcomputer.

Figure 9:
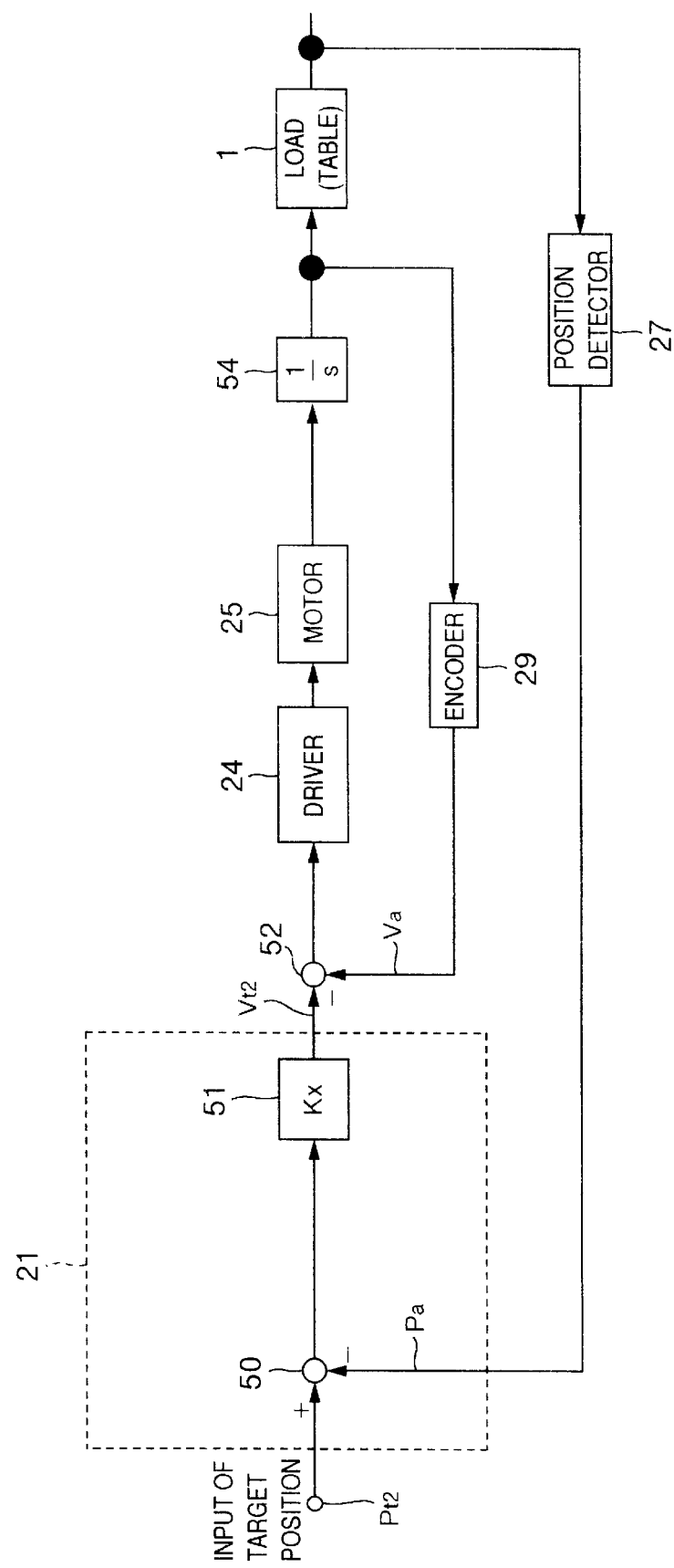
FIG. 9 is a block diagram showing a positioning servo-control system or loop for performing a table position control in the control apparatus according to the first embodiment of the invention.

Next, referring to a block diagram shown in FIG. 9, description will be directed to the positioning servo-control loop designed for performing a position control operation of the table 1 in cooperation with the table position control unit 21. The positioning servo-control loop is selected by the change-over unit 23 when the X-ray CT imaging operation is to be carried.

Referring to the figure, the positioning servo-control loop is constituted by an input unit through which a signal indicating a target or desired position is inputted (target position input $Pt_2$), a positioning servo-amplifier 51, a speed servo-amplifier 53, the motor 25, an integrator 26, the load or table 1, the table position detector 27 and the encoder 29. The positioning servo-control loop is designed to control the operation of the motor 25 such that deviation between the target position $Pt_2$ of the load or table 1 and the actual position Pa thereof can be maintained zero. The coordinate data for the X-ray CT operation are inputted as the target position ($Pt_2$) data to the positioning control loop from an input device of an operation console (not shown) installed at a remote location.

With the positioning servo-control loop shown in FIG. 9, the table 1 is automatically so controlled as to be maintained at the desired or target position $Pt_2$. Difference between the current position Pa of the table 1 as detected by the table position detector 27 and the target position $Pt_2$ can be derived from the output of an adder 50. Difference between the signal $Vt_2$ amplified with a gain Kx by the positioning servo-amplifier 51 and the negative feedback signal Va indicative of the motor speed detected by the encoder 29 is determined by an adder 52. The control loop constituted by the motor driver 24, the motor 25, an integrator 54 and the encoder 29 serves as a speed servo-control loop which is effective for maintaining the motor speed at a desired speed $Vt_2$ corresponding to the input target position $Pt_2$. When the table 1 is subjected to some external force, the motor 25 is controlled by the negative feedback signal Pa of the table position detector 27 such that the table 1 is maintained at the target position $Pt_2$.

Parenthetically, the table position control unit 21 indicated as being enclosed by a broken line block in the force control system shown in FIG. 9 may be implemented by a microcomputer which is commercially available. The microcomputer includes an input/output interface, an A/D converter for converting an analogue signal to a digital signal, a memory unit for storing a control program and coefficient data, and a CPU for executing signal processings in accordance with the control program. However, it goes without saying that the functions of the table position control unit 21 may be realized by a combination of discrete electronic circuit elements in place of the microcomputer.

The force control loop described above by reference to FIG. 8 and the positioning servo-control loop shown in FIG. 9 is designed to perform the respective controls in the X-direction. It goes however without saying that by providing the manipulating force control loop and the positioning servo-control loop in each of the X-direction and the Y-direction, there can be realized a control system which is capable of performing the table positioning control two-dimensionally (i.e., in both X- and Y-directions separately or concurrently).

Figure 10:
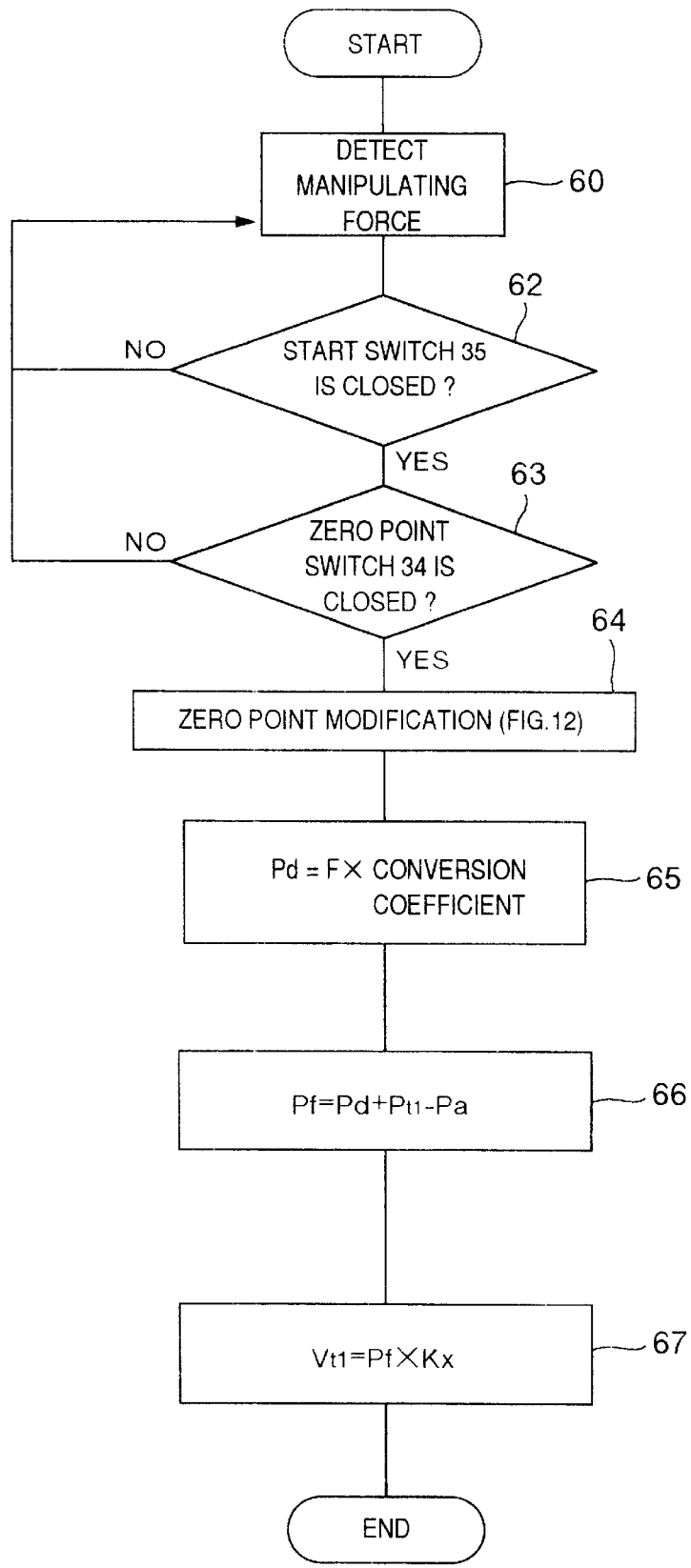
FIG. 10 is a flow chart for illustrating operations of a manipulating force control unit constituting a part of the manipulating force control loop shown in FIG. 8.

Next, operation of the manipulating force control unit 22 constituting a part of the force control system shown in FIG. 8 will be described by reference to a flow chart shown in FIG. 10. The operator applies a manipulating force onto the knob 32 of the manipulation unit 2. In a step 60, the load cell 26 detects magnitude of the manipulating force and the direction thereof to thereby output an electric signal corresponding to the manipulating force. In a step 62, decision is made as to whether or not the manipulating force detection start switch 35 is in the closed state. Unless the manipulating force detection start switch 35 is in the closed state, the step 60 is resumed. If otherwise, the processing proceeds to a step 63. In the step 63, decision is made as to whether or not the manipulating force zero point detecting switch 34 is in the closed sate. Unless the manipulating force zero point detecting switch 34 is in the closed state, the step 60 is resumed. When the manipulating force zero point detecting switch 34 is closed (i.e., when both the decision steps 62 and 63 result in affirmation "Yes"), a zero point modification processing is performed in a step 64 for setting to zero the initial manipulating force upon starting displacement of the table. In this conjunction, the zero point modification processing will be described later on by reference to FIG. 12. In a step 65, the positional displacement Pd is arithmetically determined by multiplying the manipulating force F by a conversion coefficient. The conversion coefficient of concern is read out from the memory mentioned previously in accordance with the value of the manipulating force F. Subsequently, in a step 66, the positional deviation Pf is determined on the basis of the current position Pa of the table 1, the target position $Pt_1$ (=0) and the positional displacement Pd. In a step 67, the desired speed $Vt_1$ for the motor speed servo-control loop is arithmetically determined.

As is apparent from the foregoing description, by virtue of the arrangement that the table positioning operation for the X-ray CT inspection and the table positioning operation for the angiographic inspection and treatment can be automatically changed over in response to manual operation of the manipulation unit 2 by the operator, the change-over operation can be performed without need for attention of the operator. In conjunction with the manipulating force control loop, it is to be added that detection quantity of the manipulating force applied to the manipulation unit 2 by the operator can be converted into a status quantity such as positional deviation, velocity or acceleration, for thereby controlling the manipulating force for positioning the table by arithmetically determining the control quantity on the basis of the status quantity mentioned above. By way of example, in a mode for carrying out the present invention, such a control method disclosed in Japanese Patent Application Un-examined Laid-open No. JP-A-8-280668 may be adopted. The control system taught in the above-mentioned application is implemented in the form of a position control loop or an acceleration control loop. For convenience' sake, description will be directed to the positioning control loop. According to this known control procedure, the status quantity of the force as fed back is multiplied by a conversion coefficient to thereby replace the status quantity of the force by a status quantity of displacement. By adding the displacement quantity thus determined to the positional deviation, there can be derived a positional deviation quantity. Thus, in the positioning control loop, such a driving command is issued to a driving motor control circuit which makes the positioning control deviation be zero. In this way, the manipulating force sensed upon moving of operator's hand can be compensated for.

Further, in the case of the control apparatus implemented in the structure described above, it is presumed that the operation of the table manipulating force control loop is imparted with higher priority when compared with the operation of the positioning control loop for the X-ray CT inspection. More specifically, when the operator depresses the push button 33 of the manipulation unit 2 in the state where the X-ray CT inspection mode is being validated, the change-over unit 23 validates the table manipulating force control loop with higher priority over the X-ray CT inspection to thereby drive the motor with the table manipulating force control signal Pd. In this conjunction, it is preferred to adopt such arrangement that when the operator detaches his or her hand from the knob 32, the positing control operation for the X-ray CT inspection is not validated at once but the table 1 is once held stationary at the current position.

Figure 11:
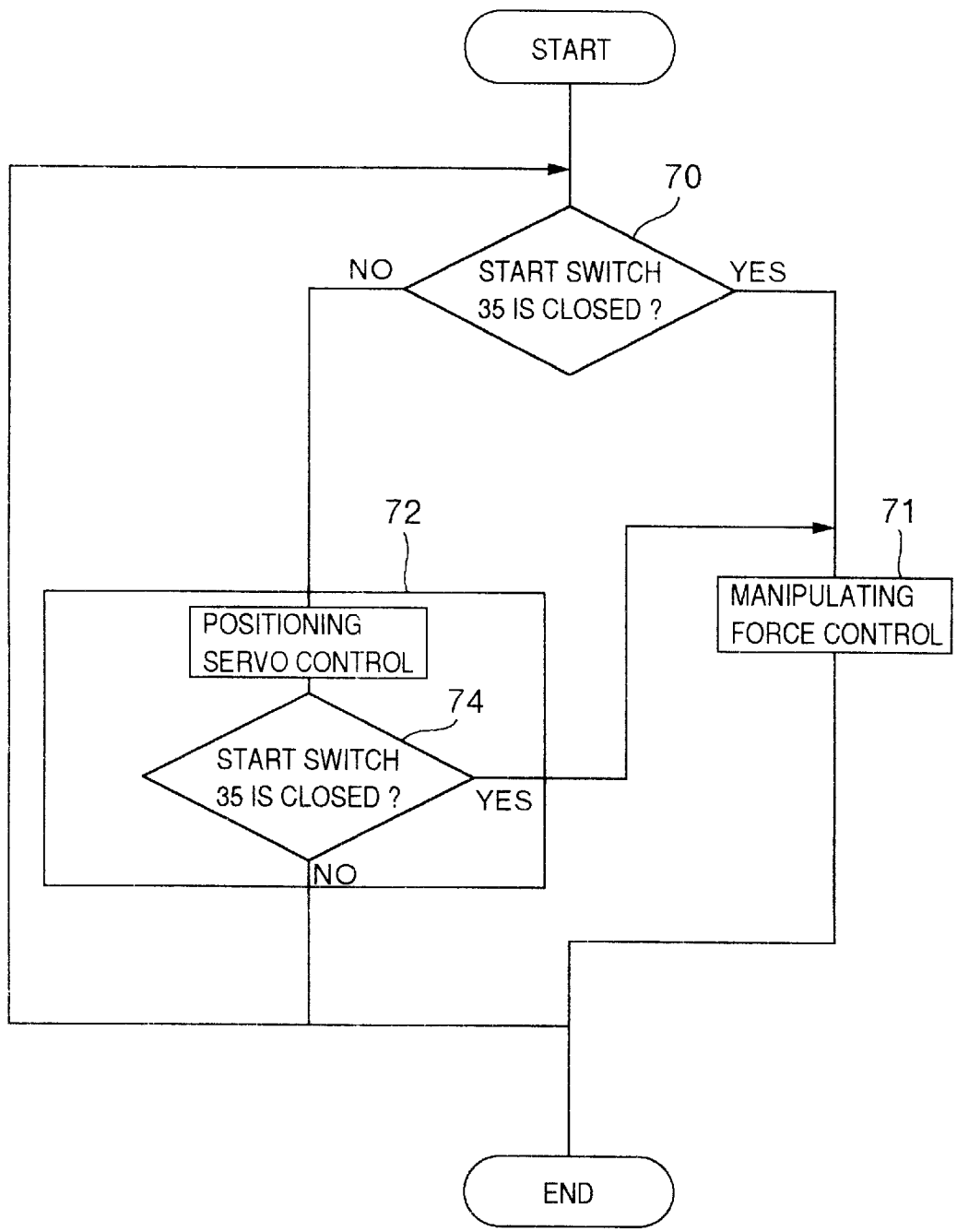
FIG. 11 is a flow chart for illustrating a processing procedure for imparting high priority to a table manipulating force control operation over a table positioning servo-control.

FIG. 11 is a flow chart for illustrating a processing procedure for imparting higher priority to the operation of the table manipulating force control loop through the medium of the change-over unit 23. In a step 70, decision is made as to whether the manipulating force detection start switch 35 is closed or not. When the switch 35 is closed, operation of the manipulating force control loop (FIG. 8) is selected. On the other hand, when the manipulating force detection start switch 35 is in the open state, operation of the positioning servo-control loop (FIG. 9) is selected. During a period in which the operation of the positioning servo-control loop is performed for the X-ray CT imaging or for other purpose, the decision step 74 is executed at appropriate time points for deciding whether the manipulating force detection start switch 35 is closed or not. When the switch 35 is closed in the course of operation of the positioning servo-control loop, the processing proceeds to the step 71 to thereby put into operation the manipulating force control loop. When it is decided in the step 74 that the manipulating force detection start switch 35 is not closed, then operation of the positioning servo-control loop is continued.

By providing the priority levels in conjunction with the control operation of the control apparatus as described above, the command for enabling operation of the manipulating force control loop can be accepted even when the positioning servo-control is being performed for the X-ray CT inspection. By contrast, so long as the operation of the table manipulating force control loop is validated, the command for enabling the operation of the positioning servo-control loop can not be accepted. By imparting higher priority to the table manipulating force control loop, such situation can be coped with successfully in which the person under inspection has to be taken out from the CT-scanner 5 for some reason when the positioning servo-control for the X-ray CT inspection is being preformed, because the table can be moved with a relatively small force as mentioned hereinbefore. Thus, safety in emergency can be enhanced significantly. Besides, by inhibiting or disabling the positioning servo-control for the X-ray CT inspection which needs accurate positional information in succession to the table manipulating force control operation, the inspection which is based on inaccurate position information can be evaded.

The output of the manipulating force detection start switch 35 is made use of as the signal for changing over the control operation between the table positioning servo-control operation for the X-ray CT inspection and the table manipulating force control operation for the angiographic inspection or treatment. With the aid of this signal, it is possible to change over the table manipulating force control operation to or from the table positioning servo-control operation without fail.

Figure 5A:
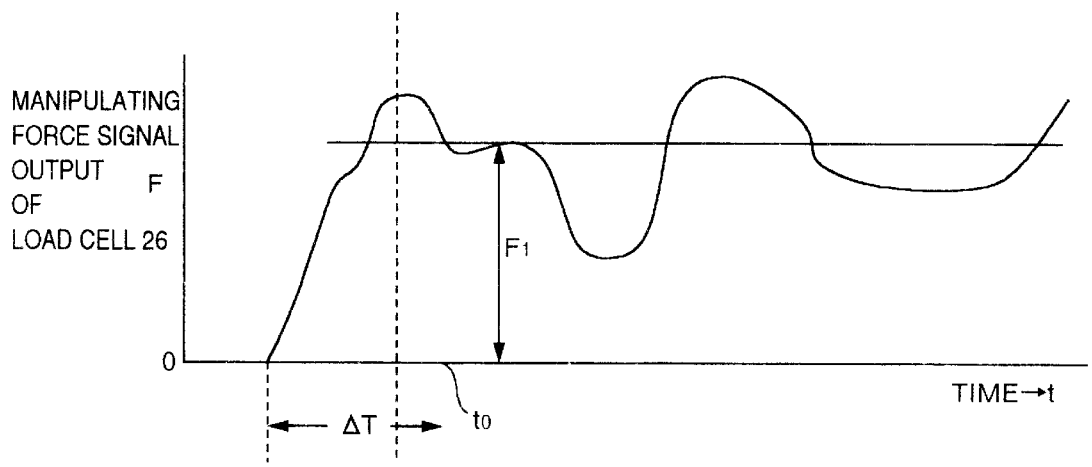
FIG. 5(A) is a waveform diagram for illustrating behavior of a manipulating force signal outputted from a load cell incorporated in a manipulation unit of the control apparatus.
Figure 5B:
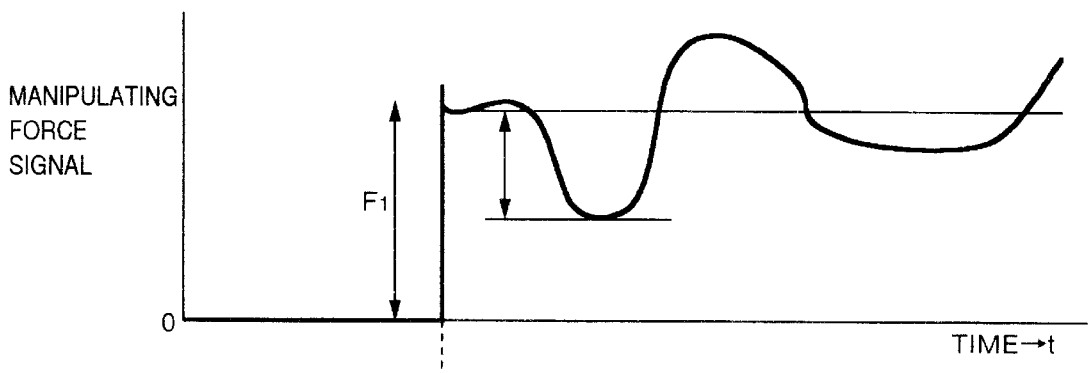
FIG. 5(B) is a waveform diagram for illustrating behavior of a manipulating force signal outputted from a load cell incorporated in a manipulation unit in another situation.
Figure 5C:
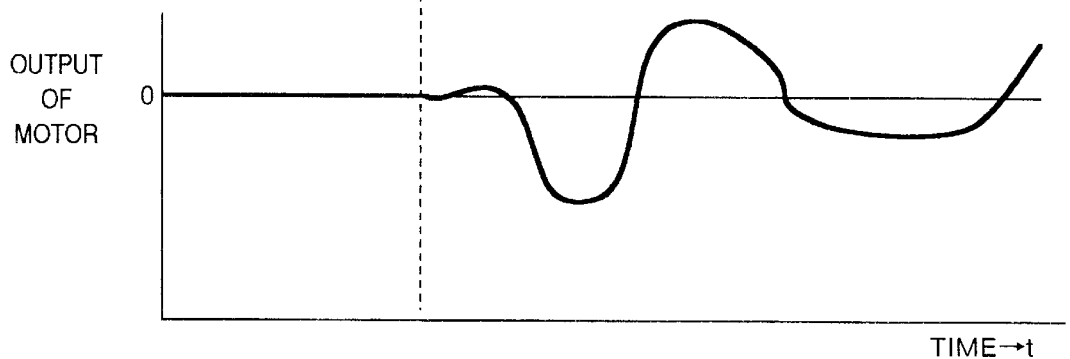
FIG. 5(C) is a waveform diagram for illustrating changes in output of a driving motor in correspondence to change of the manipulating force illustrated in FIG. 5(B)
Figure 12:
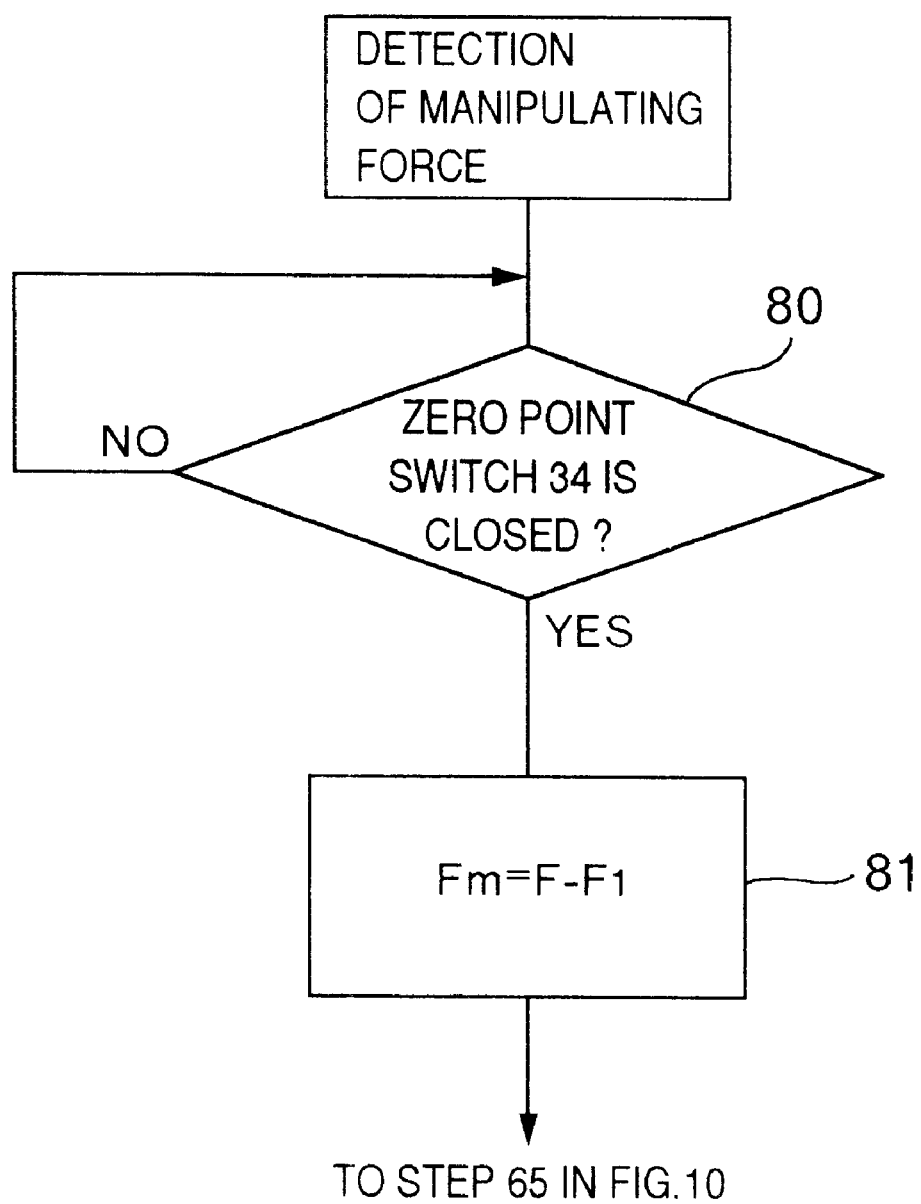
FIG. 12 is a flow chart for illustrating a processing procedure for modifying a zero point in a force-displacement conversion unit constituting a part of the manipulating force control system or loop shown in FIG. 8.

Next, the role or function of the manipulating force zero point detecting switch 34 will be elucidated by referring to FIGS. 5(A) to 5(C) together with a flow chart shown in FIG. 12. In FIG. 5(A), time is taken along the abscissa while taken along the ordinate is the output of the load cell 26 generated when the operator operates the manipulation unit 2, i.e., the manipulating force signal F. The value of the manipulating force signal F remain zero so long as the manipulation unit 2 is not touched by the operator. When the operator touches the knob 32 and applies a force, the manipulating force signal F changes, for example, in such a manner as illustrated in FIG. 5(A). As can be seen, the manipulating force signal F is outputted at a time point $t_0$ with a delay $\Delta T$ from the closure of the manipulating force detection start switch 35. At this juncture, let's represent by $F_1$, the value (absolute value) of the manipulating force when the manipulating force detection start switch 35 is closed at the time point $t_0$. In this conjunction, it is further assumed that the manipulating force has been applied to the load cell 26 when the push button 33 is depressed. In that case, the manipulating force detection signal $F_1$ may assume a large value, as shown in FIG. 5(B). Accordingly, when the motor control is performed on the basis of the manipulating force detection signal $F_1$ of large value, there may then arise such situation that the motor output increases steely, resulting in that the table 1 is moved under a manipulating force of large magnitude unexpectably for the operator. In order to avoid such situation, it is also taught by the present invention that the manipulating force detection signal $F_1$ is once set to zero at a time point when the manipulating force zero point detecting switch 34 is closed after lapse of the time $\Delta T$ from the closure of the manipulating force detection start switch 35. After the time point to, the change $\Delta F$ of the manipulating force detection signal $F_1$ is made use of as the change of the manipulating force in the manipulating force control. At this juncture, it should be mentioned that even when the operator has applied a manipulating force before the push button 33 is pushed, the table manipulating force increases only by magnitude $\Delta F$ from the manipulating force being applied at the time point when the manipulating force detection start switch 35 is closed. Accordingly, the table is protected against sudden movement. Further, it is noted that steep change of the manipulating force detection signal such as illustrated in FIG. 5(B) may lead to generation of vibration of the table itself. However, by adopting the method taught by the invention, the output of the motor changes only gently, as illustrated in FIG. 5(C), whereby vibration event of the table can positively be suppressed.

Furthermore, it should be added that because of provision of the manipulating force detection start switch 35, the table can not move even when an unintentional force is applied onto the knob 32 so long as the manipulating force detection start switch 35 is not closed, whereby the table can remain stationary, which in turn means that enhanced safety can be ensured.

FIG. 12 is a flow chart for illustrating a processing procedure for modifying the zero point in the force-to-displacement conversion unit 39. Referring to the figure, decision is made in a step 80 whether the manipulating force zero point detecting switch 34 is closed or not. If it is closed, a modified manipulating force Fm is arithmetically determined by subtracting the initial manipulating force $F_1$ from an actual manipulating force F derived from the output of the load cell 26. Subsequently, the modified manipulating force Fm determined in the step 81 is used as the manipulating force F in the arithmetic operation in the step 65 shown in FIG. 10.
Embodiment 2

Figure 6:
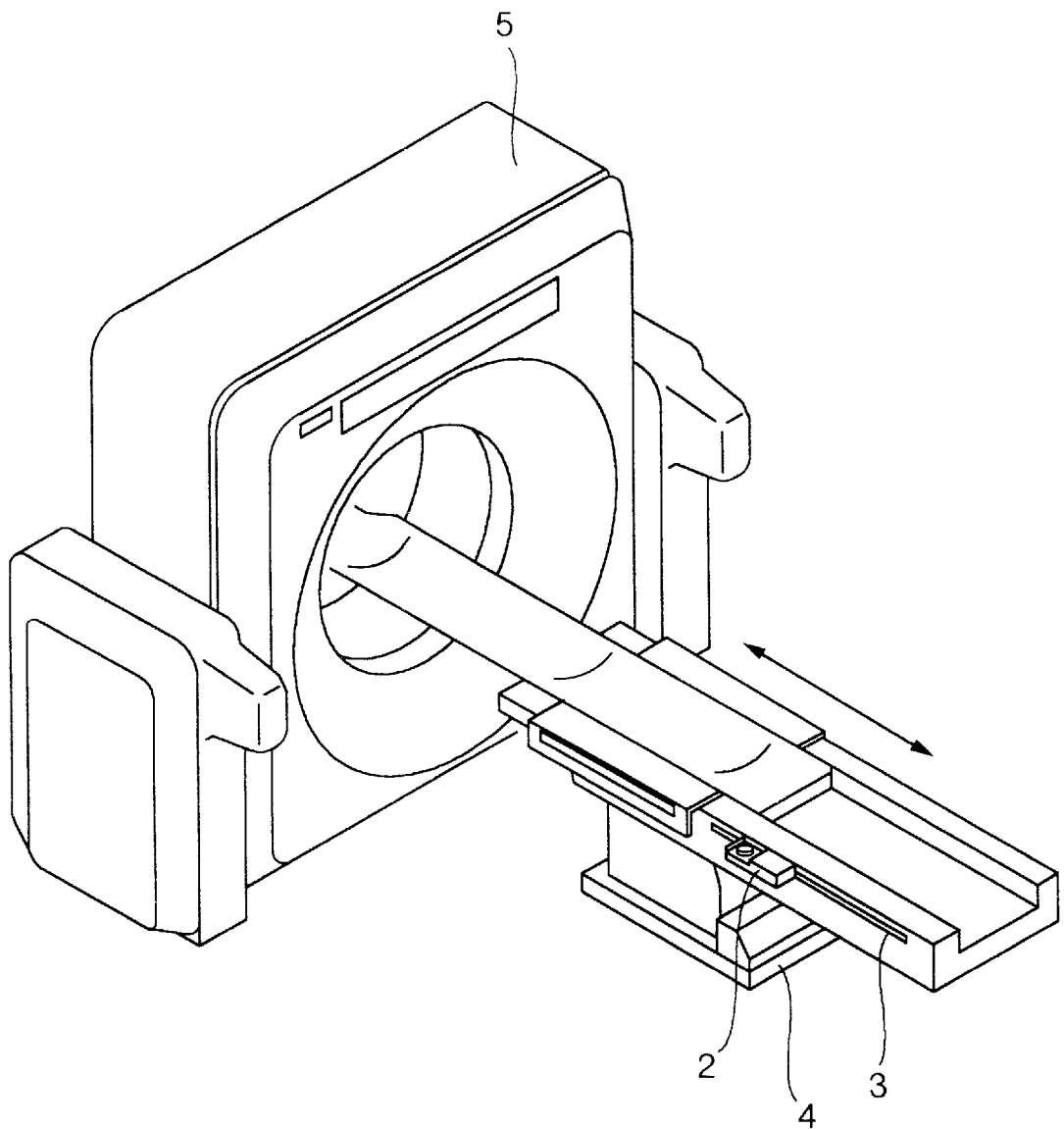
FIG. 6 is a schematic perspective view showing generally a diagnosis system equipped with an X-ray CT fluoroscopy system in which the control apparatus according to a second embodiment of the invention is employed.

Next referring to FIG. 6, description will turn to a second embodiment of the present invention. In recent years, in accompanying development of the IVR technique, the X-ray CT technology has made a great progress to such a level that diagnosis can be carried out with the aid of three-dimensional images generated by the spiral scanning operation. More specifically, for generating the three-dimensional images, the scanner 5 is moved along the table 1 at a constant speed while being rotated continuously with the X rays transmitted through an object under inspection being detected, whereon the images are reconstituted at a high speed on the basis of the detected data for allowing the CT images to be displayed sequentially for observation on a real time basis. Thus, a sort of the biopsy can be realized. This method is referred to as the CT-fluoroscopy imaging method. Since tomographic images can be observed on a real-time basis by resorting to the CT-fluoroscopy, this method is very effective for confirming the state of needle biopsy. The table used for carrying out this process is not designed for floating movement described hereinbefore in conjunction with the first embodiment but designed to be movable only in the longitudinal direction of the person lying on the table (i.e., only in the X-direction) as in the case of the conventional CT system. According to the present invention incarnated in the instant embodiment, the manipulating force control function described hereinbefore is imparted to the table used in the CT system now under consideration. Thus, there can be available not only the images taken by positioning the table in the direction orthogonal to the scanner 5 but also the images taken by positioning the table in the direction parallel to the scanner 5. This means that the range of the images which can be observed for the diagnosis or treatment is increased, which is of course very effective and advantageous for the CT-fluoroscopy diagnosis. The manipulating force control function mentioned above can be realized by disposing the manipulation unit 2 described hereinbefore on the rail 3 which extends along a lateral side of the table so that the operator can displace the table and hence a person under inspection lying thereon to a desired position. In that case, the control apparatus may be implemented substantially in the same configuration as the one shown in FIG. 2. In the control apparatus according to the instant embodiment of the invention, the priority control may also be adopted for the table displacement control similarly to the first embodiment such that the table manipulating force control can be carried out when the CT-fluoroscopy is being performed although the table positioning control for the X-ray CT inspection or diagnosis is disabled. In that case, the control apparatus should be so arranged that the table can be moved smoothly as desired by the operator for allowing a variety of tomographic images to be taken. Needless to say, possibility or capability of performing the X-ray CT-fluoroscopy during the table manipulating force control operation is very effective and advantageous for confirming the state of needle biopsy.
Embodiment 3

Figure 7:
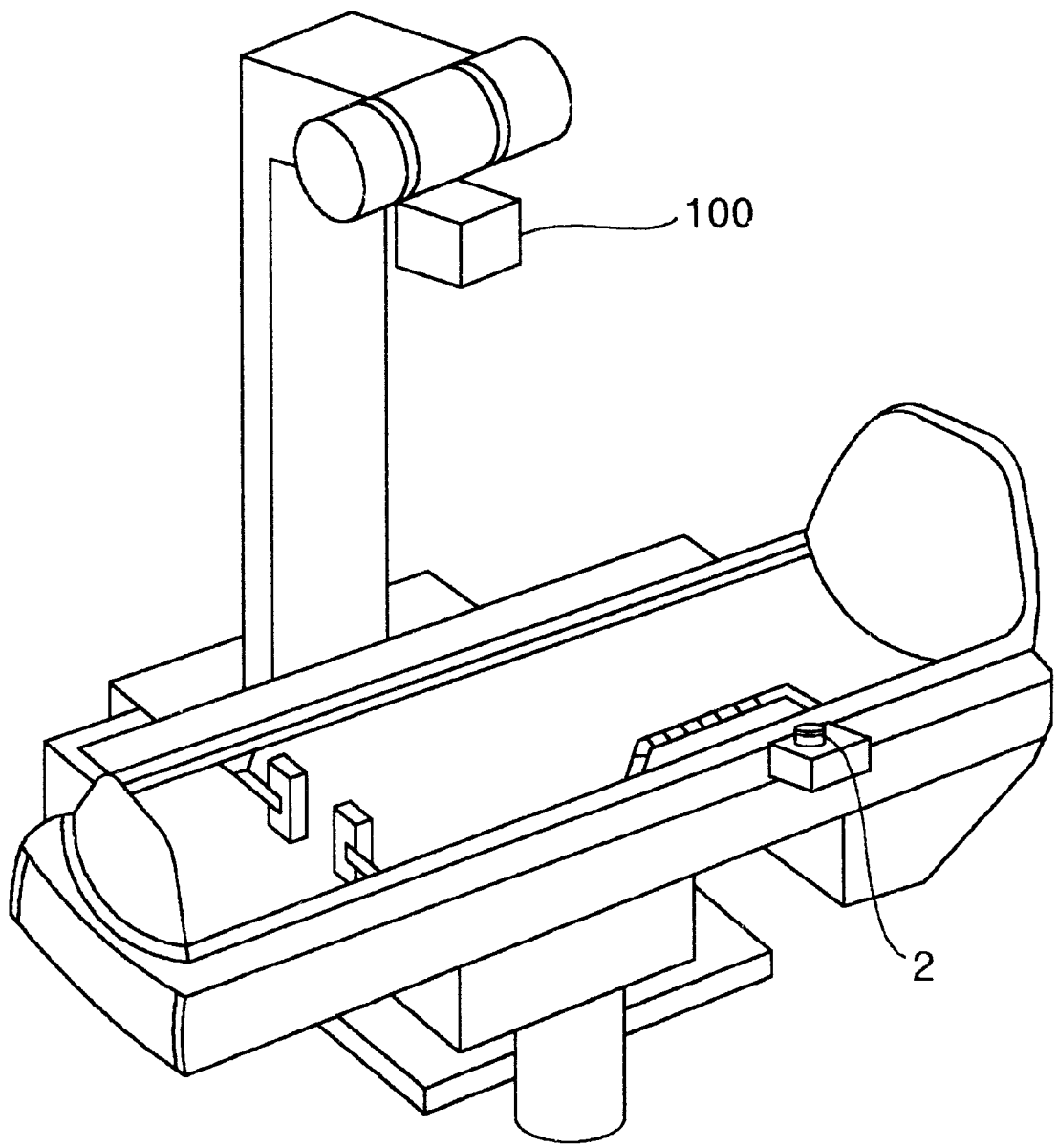
FIG. 7 is a schematic perspective view showing generally a diagnosis system equipped with an X-ray fluoroscopy/photography system in which the control apparatus according to a third embodiment of the invention is employed.

A third embodiment of the present invention is directed to an X-ray fluoroscopy system shown in FIG. 7.

The X-ray fluoroscopy photography system is employed primarily for the inspection of the alimentary canal or tract. In recent years, however, this system is used for performing the interventional radiology or IVR for the non-blood-vessel organs. In that case, the table manipulating force control function taught by the present invention can be imparted to the table so that the table and hence the person under treatment lying thereon can be positioned in alignment with e.g. the center of an image intensifier 100 constituting a major part of the imaging system. By applying the table manipulating force control taught by the invention, the table can be displaced to a desired position smoothly with a manipulating force of small magnitude.

Thus, in the X-ray fluoroscopy/photography system according to the instant embodiment of the invention, the manipulation unit 2 is mounted on a rail extending along each lateral side of the table so that the floating table manipulation operation can be realized in the X- and Y-directions as described hereinbefore in conjunction with the first embodiment. However, in the case of the X-ray fluoroscopy/photography system, blurs may occur in the images and/or the X-ray photographs if the table manipulating force control operation is performed when the imaging operation is being carried out. Accordingly, such priority control is adopted that the table manipulating force control operation is inhibited during the imaging operation by making use of the table control change-over unit described herein before.

Embodiment 4

Figure 13:
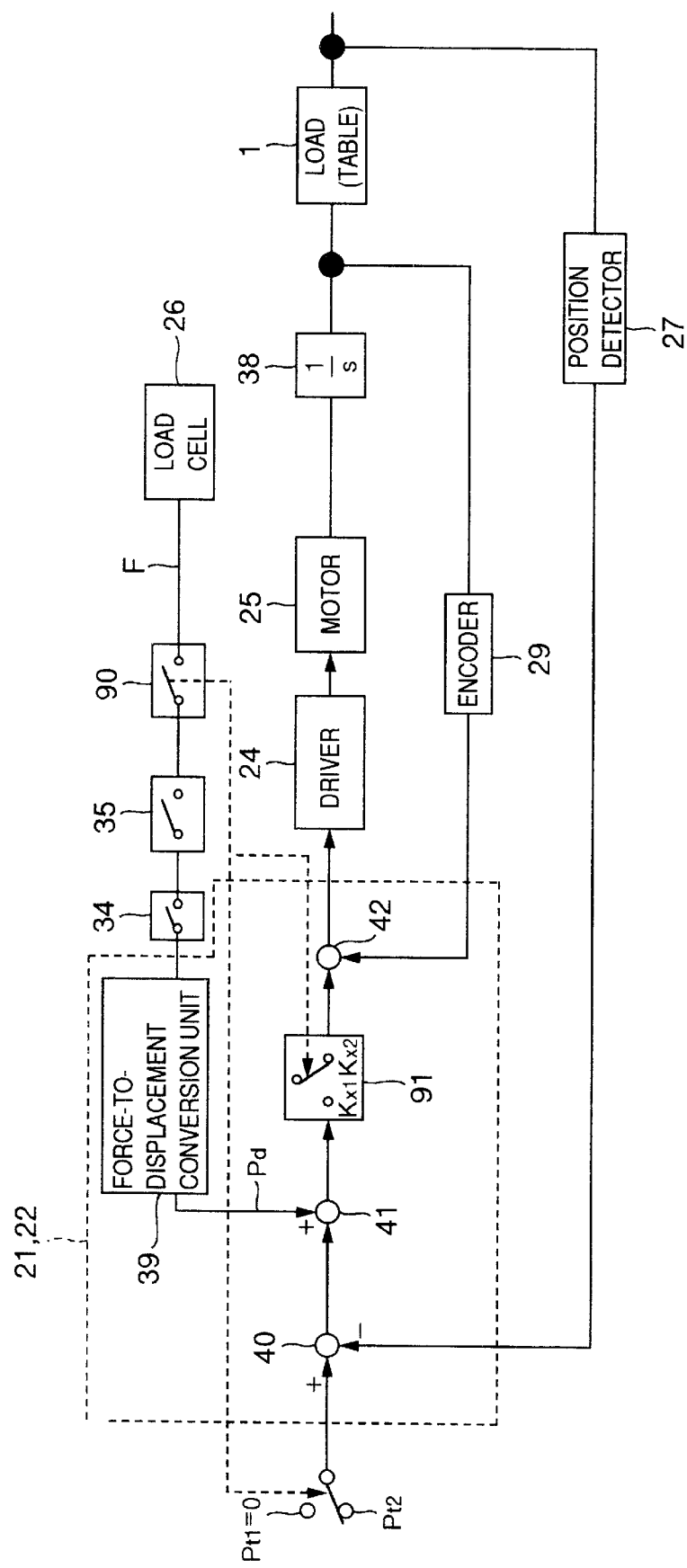
FIG. 13 is a diagram showing a configuration of the control apparatus according to a fourth embodiment of the present invention.

Description will now be directed to a fourth embodiment of the present invention by reference to FIG. 13. As can be seen by comparing the manipulating force control system shown in FIG. 8 with that of the positioning servo-control system shown in FIG. 9, there exist fundamental blocks common to both of these control systems. By way of example, the control loops including the amplifiers 37; 51, the driver 24, and the integrators 38; 54 are common to both the manipulating force control system and the positioning servo-control system. According to the teaching of the invention incarnated in the fourth embodiment, these common control loops are implemented in one unit designed to be shared by the manipulating force control system and the positioning servo-control system.

In FIG. 13, same functional elements as those shown in FIG. 8 are denoted by like reference numerals. Further, in FIG. 13, the functional elements denoted by same reference numerals used in FIG. 8 or 9 are same as those described hereinbefore, and repeated description thereof is omitted. A switch 90 is incorporated in the change-over unit 23 for changing over the manipulating force control system and the positioning servo-control system. In the state shown in FIG. 13, toe switch 90 is opened, whereby the positioning servo-control system for the X-ray CT is selected. In that case, the desired position is changed over to the desired position $Pt_2$ for the positioning servo-control system in interlocking with the opening of the switch 90 and at the same time the gain of a positioning servo-amplifier 91 is changed over to $Kx_2$. Thus, the control apparatus automatically controls the table 1 so that it is maintained at the desired position $Pt_2$.

When the manipulating force control system is selected by closing the switch 90, the manipulating force signal F derived from the output of the load cell 26 is inputted to the force-to-displacement conversion unit 39 in the state in which the switches 34 and the 35 are closed, whereby a control quantity Pd is outputted from the force-to-displacement conversion unit 39. At the same time, the desired position input is changed over to the value $Pt_1$ (=0). Furthermore, since the dynamic range of the manipulating force control system differs from that of the positioning servo-control system, the gain of a positioning servo-amplifier 91 is also changed over to a value $Kx_1$. In that case, the table 1 is moved in conformance with the manipulating force F applied by the operator under the control of the control apparatus.

Turning back to FIG. 2, the block diagram shown therein is so depicted that bidirectional signal transmission can take place between the table position control unit 21 and the change-over unit 23. The signal for the positioning servo-control is transmitted to the change-over unit 23 from the table position control unit 21. On the other hand, transmitted to the table position control unit 21 from the motor driver (servo-amplifier) 24 by way of the change-over unit 23 is an error signal. Further, bidirection signal transmission can equally take place between the manipulating force control unit 22 and the change-over unit 23. The control signal for the force control is transmitted to the change-over unit 23 from the manipulating force control unit 22. On the other hand, an error signal is transmitted to the manipulating force control unit 22 from the motor driver 24 by way of the change-over unit 23. Additionally, the bidirection signal transmission can take place between the change-over unit 23 and the motor driver 24 as well. Transmitted to the motor driver 24 from the change-over unit 23 is a speed control signal. The driving signal of the motor and the error signal outputted from the amplifier are transmitted to the change-over unit 23 from the motor driver 24.

Figure 14:
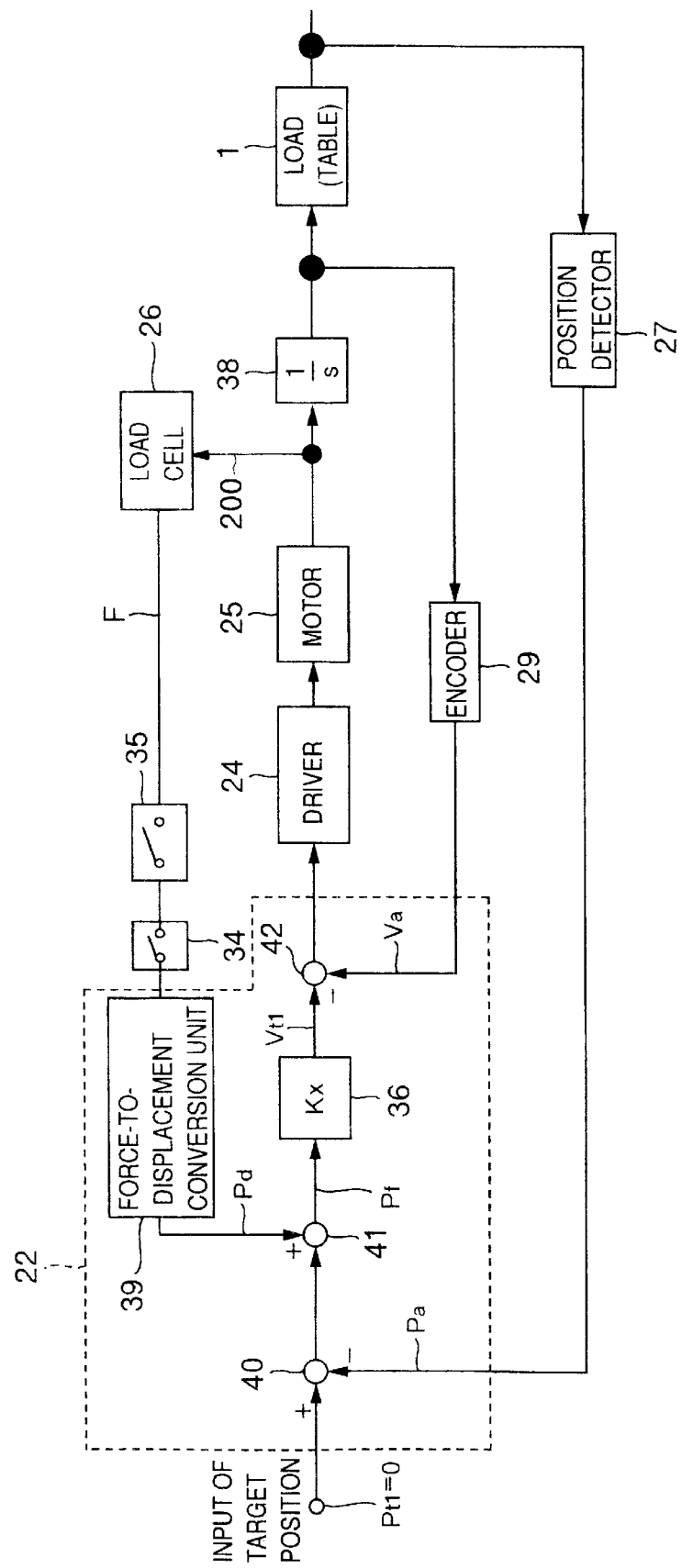
FIG. 14 is a block diagram showing a manipulating force control system having a force feed-back loop.

FIG. 14 shows a manipulating force control system which is basically same as the control system shown in FIG. 8. The arrow 200 from the output of the motor 25 to the load cell 26 represents a force feed-back. The load cell 26 (manipulation knob 32) is mounted on the rail 3 of the table 1, and is movable along with moving of the bed 1 driven by the motor 25. When the table 1 moves, the load cell 26 also moves. Then the operator follows the moving of the load cell 26 (manipulation knob 32) by moving his hand. The move of the operator's hand gives corresponding force (a force feed-back) to the load cell 26. This force feed-back causes a natural feeling of manipulation to the operator.

Many features and advantages of the present invention are apparent from the detailed description and thus it is intended by the appended claims to cover all such features and advantages of the system which fall within the true spirit and scope of the invention. Further, since numerous modifications and combinations will readily occur to those skilled in the art, it is not intended to limit the invention to the exact construction and operation illustrated and described.

By way of example, the time difference ΔT intervening between the operation of the switch 34 and that of the switch 35 may equally be set to an appropriate value by adopting a timer circuit. Furthermore, the push button 33 and the knob 32 of the manipulation unit 2 may be implemented in such a structure that the manipulation unit 2 can be actuated by other part of the operator such as a foot or the like. Additionally, the manipulation unit 2 may be disposed at a location remote from the table 1. In other words, the manipulation unit 2 may be so implemented as to be controlled through remote control by way of a transmission path.

In the above mentioned embodiments, either one of two control systems including a position servo-control system and a force control system is selectively activated. For example, the position servo-control system is activated for X-ray CT operation, and the force control system is activated for angiographic inspection. However, according to the present invention, combination of two control systems can be used only for X-ray CT operation or for angiographic inspection. For example, for table positioning operation in X-ray CT operation, the table is controlled with the force control system and while the position servo-control system is operating.

Furthermore, although it has been assumed in the foregoing description that the present invention is applied to the X-ray imaging system and the X-ray CT system, it goes without saying that the present invention can find application to the control of a table (i.e., member for supporting a person lying thereon) in any other medical diagnosis systems in which the table positioning control and the table manipulating force control are required.

Accordingly, all suitable modifications and equivalents may be resorted to, falling within the spirit and scope of the invention.

With the arrangements of the control apparatus described above, there can be achieved advantageous effects and actions mentioned below.

(1) Because the table is imparted with the manipulating force control function (22), the operator can displace the table to a desired position with a relatively small manipulating force while ensuring enhanced manipulation performance.

(2) By virtue of the arrangement that the manipulating force control function (22) is added to the conventional table position control function (21) so that they can be exchanged by means of the change-over unit 23, the manual table positioning to a desired position can be realized in addition to the conventional high-speed positioning function. Thus, the control apparatus according to the present invention can find a wide range of applications such as imaging, photographing, inspection, diagnosis, therapy, etc.

(3) In particular, in a system in which the X-ray CT system and an angiographic system are combined together for performing consistently from the diagnosis to the therapy by taking advantage of the feature mentioned in the above paragraph (2), one and the same table can be used not only for the X-ray CT but also for the angiography. Thus, the person under treatment can remain lying on the same table to undergo the different diagnoses.

(4) By imparting higher priority to the table manipulating force control than the table positioning control, it is possible to move the table with ease for taking out the person under treatment in emergency even during the positioning control for the inspection with the X-ray CT system. Thus, enhanced safety can be assured even in case of emergency.

(5) Furthermore, owing to such arrangement that the two switches, i.e., the manipulating force detection start switch 35 and the manipulating force zero point detecting switch 34 are provided as the operator's manipulating force detecting means, wherein the manipulating force zero point detecting switch 34 is turned on after lapse of a predetermined time ΔT from the closing of the manipulating force detection start switch 35 for validating the manipulating force detection signal, the manipulating force detection signal is protected against rapid or steep change even when the manipulating force input signal changes remarkably, which is very effective for suppressing shaking or vibration of the table.

What is claimed is:

1. A control apparatus for controlling movement of a table supporting an object in a medical diagnosis system, comprising:

driving power means for moving said table in a predetermined direction;

position detector means for outputting a position signal corresponding to a position of said table;

positioning servo-control means for controlling said driving power means so that said position signal coincides with a given desired value;

manipulating force detector means for outputting a force signal corresponding to a manipulating force applied by an operator;

force-to-position conversion means for converting said force signal into a position chance quantity for said table;

force control means for controlling said driving power means in accordance with said position chance quantity so long as said manipulating force of said operator is being detected; and change-over means for selecting either said positioning servo-control means or said force control means in response to operation of said operator.

2. A control apparatus according to claim 1, further comprising:

detecting means for detecting start of operation performed by said operator, wherein said change-over means is so arranged as to put into operation said force control means upon detection of the start of operation of the operator by said manipulating force detector means when said positioning servo-control means is selected, while said positioning servo-control means can be selected so far as the start of operation of said operator is not detected by said manipulating force detector means.

3. A control apparatus according to claim 1, further comprising:

detecting means for detecting start of operation by said operator; and input means for inputting said force signal to said force-to-position conversion means with delay of a predetermined time from detection of the start of operation of said operator.

4. A control apparatus according to claim 3, further comprising:

means for stopping transmission of said force signal to said force-to-position conversion means in dependence on operation performed by said operator; and detecting means for detecting end of operation of said force control means with delay of a predetermined time from the stoppage of transmission of said force signal.

5. A control apparatus according to claim 1, further comprising:

a first switch for turning on/off a signal path extending between said manipulating force detector means and said force-to-position conversion means; and a second switch connected in series to said first switch by way of said signal path and operating with a time difference relative to operation of said first switch, wherein said first switch is closed in response to the start of operation performed by the operator while said second switch is closed with delay of a predetermined time from closure of said first switch to thereby allow said force signal to be inputted to said force-to-position conversion means, whereas said second switch is opened in dependence on operation performed by said operator to thereby stop transmission of said force signal to said force-to-position conversion means while said first switch is opened with delay of a predetermined time from the opening of said second switch to thereby terminate operation of said force control means.

6. A control apparatus according to claim 5, further comprising:

manipulating means including an integral combination of a manipulating force transmission member for operating said first switch and said second switch in response to motion of a hand or a part of body of the operator and said manipulating force detector means for detecting magnitude of a manipulating force and a direction thereof on the basis of the motion of the hand or a part of body of said operator.

7. A control apparatus according to claim 6,
wherein said manipulating means is installed on said table.

8. A control apparatus according to claim 6, said manipulating means being installed at a place remote from said table, said apparatus further comprising:
means for transmitting a signal from said manipulating means to said force control means.

9. A control apparatus according to claim 1,
wherein said force-to-position conversion means is so arranged as to set a value of said force signal detected initially to zero and then convert difference in value between a force signal detected at first after said zero setting and a force signal detected in secession into said position change quantity.

10. A control apparatus according to claim 1,
wherein said positioning servo-control means and force control means shares a common control circuit with each other,
said common control circuit includes:
error signal output means for outputting an error signal corresponding to difference between said desired value of the position and said position signal;
servo-control means for controlling said driving power means in accordance with said error signal to thereby maintain said error signal at a predetermined value; and
change-over means for selectively actuating either said force control means or said positioning servo-control means by coupling or decoupling said manipulating force detector means and said force-to-position conversion means to or from said common control circuit.

11. A control apparatus according to claim 10,
wherein said change-over means includes:
means for changing said desired value of position and gain of said servo-control means of said common control circuit in dependence on change-over between said force control means and said positioning servo-control means.

12. A control apparatus for controlling movement of a table supporting an object in a medical diagnosis system, comprising:
driving power means for moving said table in a predetermined direction;
position detector means for outputting a position signal corresponding to a position of said table;
manipulating force detector means for outputting a force signal corresponding to a manipulating force applied by an operator; and
control means including first and second control system.

13. A control apparatus according to claim 12, wherein said control means selects either one of said first and second control systems in response to operation of the operator, said first control system controls said driving power means so that said position signal coincide with a given desired value, and said second control system controls said driving power means in accordance with a position change quantity so long as said manipulating force of said operator is being detected.

14. A control method for controlling movement of a table supporting an object in a medical diagnosis system, comprising the steps of:
generating a position signal corresponding to a position of said table;
executing a positioning servo-control for controlling said driving power means coupled to said table so that said position signal coincides with a given desired value;
detecting a manipulating force applied by an operator for outputting a force signal corresponding to said manipulating force;
converting said force signal into a position change quantity for said table;
executing a force control for controlling said driving power means in accordance with said position change quantity so long as said manipulating force of said operator is being detected; and
selecting either said positioning servo-control or said force control in response to operation of said operator.

15. A control method according to claim 14, further comprising:
a step of detecting start of operation performed by said operator,
wherein in said start force cog step, said force control is exchangeably put into operation upon detection of the start of operation of said operator when said positioning servo-control is selected, and wherein said positioning servo-control is selectively put into operation so far as the start of operation of said operator is not detected.

16. A control method according to claim 11, further comprising:
a step of detecting start of operation performed by said operator; and
a step of converting said force signal into said position change quantity with delay of a predetermined time from detection of the start of operation of said operator.

17. A control method according to claim 16,
wherein conversion of said force signal into said position change quantity is stopped in dependence on operation performed by said operator, and wherein operation of said force control is terminated with delay of a predetermined time from the stoppage of conversion of said force signal.

18. A control method according to claim 11,
wherein in said force control, a value of said force signal detected initially is set to zero and then difference in value between a force signal detected at first after said zero setting and a force signal detected in secession is converted into said position change quantity.

* * * * *